Figure 1:
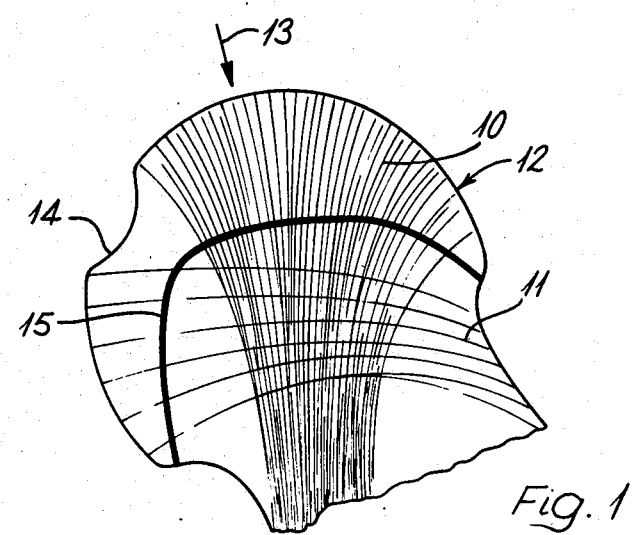

United States Patent [19]

Field

[11] Patent Number: 4,662,888

[45] Date of Patent: May 5, 1987

[54] ENDOPROSTHETIC BONE JOINT COMPONENTS

[75] Inventor: Richard E. Field, Cambridge, England

[73] Assignee: National Research Development Corporation, London, England

[21] Appl. No.: 760,589

[22] Filed: Jul. 30, 1985

[30] Foreign Application Priority Data

Aug. 1, 1984 [GB] United Kingdom ............... 8419559

[51] Int. Cl.⁴ ............................ A61F 2/30; A61F 2/36; A61F 2/38
[52] U.S. Cl. ....................................... 623/16; 623/20; 623/23; 128/92 VV; 128/92 VW
[58] Field of Search ................ 623/23, 22, 16, 18; 128/92 CA

[56] References Cited

U.S. PATENT DOCUMENTS

| | | | |
|---|---|---|---|
| 3,893,196 | 7/1975 | Hochman | 623/23 X |
| 4,312,079 | 1/1982 | Dorre et al. | |
| 4,532,660 | 8/1985 | Field | 128/92 CA X |
| 4,547,910 | 10/1985 | Roberts et al. | 623/23 X |

FOREIGN PATENT DOCUMENTS

| | | |
|---|---|---|
| A10017930 | 10/1980 | European Pat. Off. |
| A10051729 | 5/1982 | European Pat. Off. |
| A20094829 | 11/1983 | European Pat. Off. |
| A10146192 | 6/1985 | European Pat. Off. |
| 2933174 | 4/1980 | Fed. Rep. of Germany |
| WO81/00808 | 4/1981 | World Int. Prop. O. |
| 1506306 | 4/1978 | United Kingdom |
| A2045082 | 10/1980 | United Kingdom |

OTHER PUBLICATIONS

Composites, vol. 5, No. 4, Jul. 1974, pp. 151–156.
Physics in Medicine & Biology, vol. 25, No. 4, Jul. 1980, pp. 611–636.

*Primary Examiner*—Richard J. Apley
*Assistant Examiner*—Alan W. Cannon
*Attorney, Agent, or Firm*—Cushman, Darby & Cushman

[57] ABSTRACT

A prosthetic component (20; 30) for replacing a region of a bone including an articular surface (12) of a joint has a first surface shaped to approximate the articular surface, and a second surface (23; 33) shaped to extend substantially perpendicularly to the principal trabecular structure (10, 11) in a section through the bone when the first surface replaces the articular surface. In the case of a long bone the second surface is preferably shaped to approximate the fused epiphyseal plate scar (15) of the bone region in question. Also the component preferably has varying elastic modulus, at least in the portion thereof bordering the second surface, to simulate that of the bone replaced thereby.

8 Claims, 8 Drawing Figures

ENDOPROSTHETIC BONE JOINT COMPONENTS

The initial basis for the present invention is the belief that a vital factor in the maintenance of normal structure in any bone is the maintenance of what can be termed a normal stress environment. Alterations of the stress environment are known to result in secondary changes to the structure of the bone. With the notable exceptions of fracture repair and exercise induced hypertrophy, such changes are almost inevitably deleterious. Accordingly if it is intended to replace a degenerate part of a bone with an endoprosthetic component, it can be argued that the structural integrity of the adjoining remnant will be best maintained by subjecting it to as normal a stress environment as possible.

Consideration of the various forms of components currently used in bone joint prostheses indicates that normal stress environments are not maintained. This is one reason, among others, why there is a continuing effort to produce components of improved performance in terms of useful life relative to difficulties such as failure due to loosening.

An object of the present invention is to further this effort by providing components which are specifically adapted to maintain a more normal stress environment than has been the case to date.

As a first step to this end there is provided a prosthetic component for replacing a region of a bone including an articular surface of a joint, such component having a first surface shaped to approximate said articular surface, and a second surface shaped to extend substantially perpendicularly to the principal trabecullar structure in a section through said bone when said first surface replaces said articular surface.

This first step is based on the view that the pattern of the stress environment in a bone will depend upon, and so correlate with, that of the trabecullar structure in the bone. More specifically this pattern is seen to be ordered rather than random, with the lines of stress due to the combination of body weight and muscle actions coinciding with the trabecullar orientation. Further use of the proposed second surface shaping to interface with the bone will give rise to application of stresses to the adjoining bone in a similar manner. Moreover, these last stresses will be predominantly compressive in nature and thus minimise those shear forces at the component/bone interface which are considered to contribute to component loosening. This is particularly relevant to the long bone joints of the lower limb where loading forces can reach up to ten times body weight.

In the case of long bones the interface surface shaping preferably approximates the fused epiphyseal plate scar adjacent the joint in question. This scar can be seen to conform to the above requirement for perpendicularity relative to the trabecullar columns and entails additional benefits for the following reasons. Firstly, when a joint component is deployed to replace irreversibly damaged bone including the articular surface it seems inappropriate, if not positively undesirable, to excise more bone than is necessary for this purpose and in this respect it is noted that irreversible bone degeneration requiring replacement does not commonly extend beyond the scar. At the same time the scar normally represents a natural division between arterial blood supplies in the bone and so excision of bone to the scar will leave the remaining bone supplied in a relatively normal manner to enhance the prospects of continuance in a healthy condition.

This is not to say that a component according to the invention should only involve replacement of bone up to the scar from the articular surface, but the component will generally extend to the scar or beyond.

As a further step towards the above objective, a component according to the invention preferably also has, in the region of its interface with the bone, a varying elastic modulus configuration generally to simulate that of the bone material replaced thereby.

The basis for this further step in the invention is that the normal stress environment not only entails a particular pattern for a given bone part in terms of orientation, but also a variation in terms of density. This last variation can be seen to correlate with a variation in the elastic modulus of the bone material and it seems appropriate to adopt a corresponding modulus variation at least through that portion of the component which is to adjoin the bone. If this is not done it is probable that loads on the component during use will give rise to excess stress in the adjoining bone material of lower modulus and this will lead, in time, to degeneration of such material and component loosening.

There are other bone material characteristics than elastic modulus which vary in a manner related to trabecullar structure, such as fatigue strength and fracture strength, but simulation of these in a replacement component is not though to be essential to the creation of a normal stress environment in the adjoining bone. It is nevertheless possible, of course, that a chosen mode of fabrication to provide the preferred modulus simulation will, at the same time, lead to simulation of other characteristics. A component according to the invention should, in any case, be adequate in respect of these and further characteristics, such as biocompatibility, which are pertinent to bone replacement.

Figure 2:
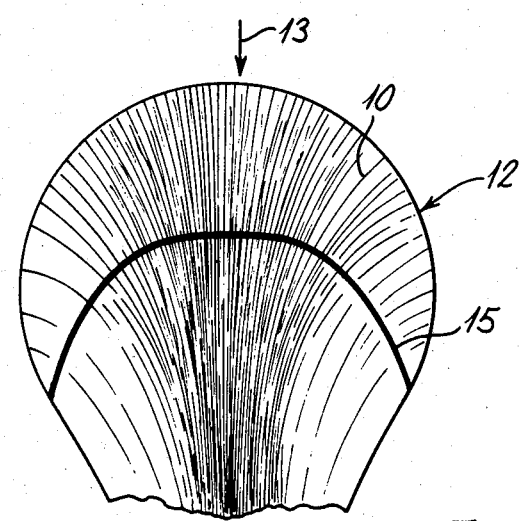
Figure 3:
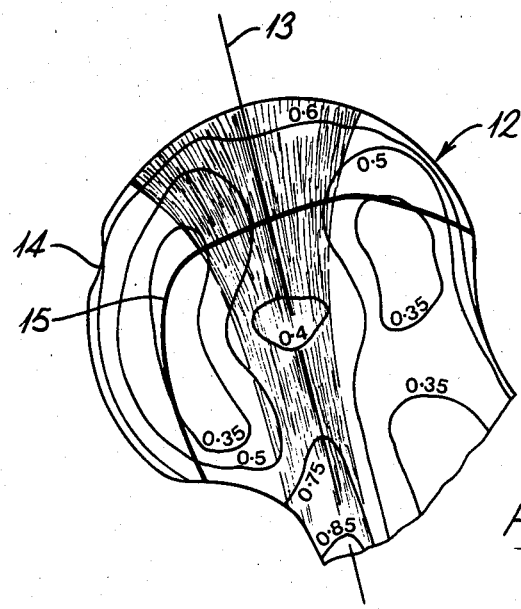
Figure 4:
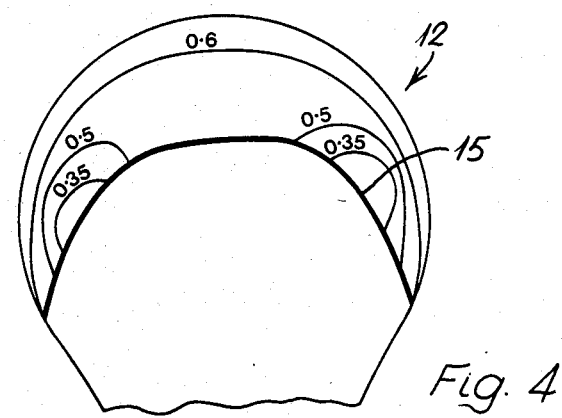
Figure 5:
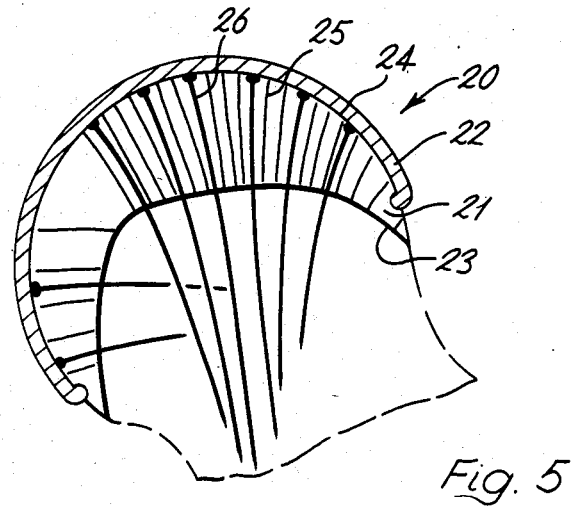
Figure 6:
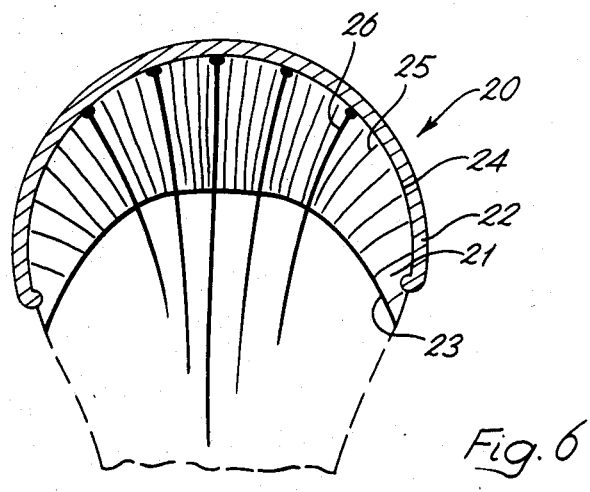

Because it is the most commonly replaced bone prt, the part of the femur at the hip joint, usually referred to as the femoral head, has been the dominant subject to date of the study leading to the development of the present invention. For the same reason it is expedient to clarify the invention further in relation to the femoral head in the following description, such description making reference to the accompanying drawings, in which:

FIGS. 1 and 2 respectively schematically illustrate the principal trabecullar structure as seen in coronal and sagittal sections of a mature femoral head;

FIGS. 3 and 4 similarly illustrate elastic modulus variations in such sections;

FIGS. 5 and 6 similarly illustrate one form of femoral head component according to the invention; and FIGS. 7 and 8 again similarly illustrate another such form.

FIGS. 1 and 2 indicate the main groups 10 and 11 of trabecullae in the femoral head 12. The group 10 is the principal compressive group through which the resultant load 13 at the head due to body weight and muscular force can be shown normally to pass. This group extends from the medial cortex of the femoral shaft to the femoral head in slightly curved lines which diverge to embrace the articular area, and they are among the densest trabecullae in the proximal femur. The group 11 is the principal tensile group and extends from the lateral cortex immediately below the greater trochanter to curve upwardly and inwardly across the neck of the femur to terminate in the medially inferior portion of the head below the fovia capitis 14. This group is thought to stabilise the head against the tendency to flattening which may otherwise occur under load, the articular surface of the heat being normally of substantially spherical shape.

These Figures indicate the general pattern of the principal trabecullar distribution to have a densest region formed by the group 10 which rises, before diverging to the articular area, as a column with a transverse configuration which is elongated anteroposteriorly, with a slight anterior bias. The lowest density region circumscribes the column of group 10 and is bounded outwardly of this group by the tensile group 11 and the cortex, while being of increased cross-sectional extent laterally and medially of the column.

FIGS. 1 and 2 also indicate the fused epiphyseal plate scar at 15. This is seen to cross the illustrated groups 10 and 11 substantially perpendicularly. Unlike the articular surface the scar is not of spherical shape but is more generally of an ovoid shape. The scar also, as noted earlier, forms a natural division by the plate between the neighbouring epiphyseal and metaphyseal arteries.

FIGS. 3 and 4 illustrate, in sections respectively corresponding to those of FIGS. 1 and 2, the general pattern of variation of elastic modulus through the bone material of the femoral head in relation to superior-inferior loading. This pattern is indicated by way of contours for successive discrete values of elastic modulus scaled between 0 and 1.0, where 1.0 represents cortical bone with a modulus normally of about 10 to 15 GPa. The contours are drawn throughout the head in FIG. 3, but only down to the scar 15 in FIG. 4, but are seen to correlate well with the trabecullar distribution discussed above.

Turning now to the embodiments of FIGS. 5 to 8, these are similar to the extent that they each have an external surface composed of an articulatory portion of spherical shape and a bone-interfacing surface shaped substantially as the epiphyseal plate scar 15. The differences between these embodiments involve the respective constructions within their similar overall shape.

The component of FIGS. 5 and 6 is denoted generally as 20 and is of two-part construction involving an inner part 21 to interface with the bone and an outer capping part 22 to provide the articulatory surface. The inner part 21 is a body of generally crescent shape in cross-section defined between a lower surface 23 approximating the epiphyseal plate scar 15 and an upper surface 24 of spherical shape.

The part 21 is to be made by moulding a plastics material of low elastic modulus around fibres 25 of the same or a compatible material of higher elastic modulus but which cannot itself be moulded. The fibres are distributed in a similar manner to that of the principal trabecullar structure and this, together with the different elastic moduli of the fibres and encapsulating moulded material, is such as to produce a three dimensional variation in overall modulus for the body similar to that of the bone replaced thereby.

One point to note concerning the modulus variation is that while such variation is to simulate that of the replaced bone, the latter variation is likely to have changed to some degree in association with the degeneration which it is intended shall be rectified. In the femoral head this last change can be shown to involve a compaction of the high modulus region represented by the principal compression group 10. This change is not normally major, but it may be appropriate to model the modulus variation of the replacement on a compromise between that of a healthy bone and that of a bone requiring replacement to enhance the provision of an optimal stress environment for the bone to be treated.

In this connection it is to be noted that the overall resultant variation in modulus can suitably vary from about 1 to 20 GPa, with the main body material being of a modulus towards the bottom of this range, and the fibres being of a modulus towards or in excess of the top of this range. A material suitable for this purpose is typically a polymer normally available in a low modulus form, but for which a drawn or other high modulus form is also available. Also, it is to be noted that the fibres of the body need not terminate at or within its surfaces, but may project to a very small extent so as to impinge on the adjoining bone and/or outer part 22 and provide a keying mechanism.

The outer part 22 can be made of the same high modulus material as the fibres, or some other appropriate material for the purposes of articulation, and is connectable with the inner part by a snap-fit thereover or in any other suitable manner.

Securement of the component with the bone preferably involves the use of filaments 26 in accordance with U.K. Patent Specification No. 2,120,103A. For this purpose the inner part 21 is formed with passageways, countersunk at the upper surface, for receipt of headed filaments to penetrate the bone, with the outer part being connected thereafter to trap the filament heads.

Shaping of the femoral head prior to fixation is suitably effected with appropriate tools deployed with reference to a guide member inserted into the bone along the load line 13 or other datum. In this connection it is noted that the scar 15, and so the component surface 23 and complementary shaping of the head, can be approximated by a succession of surfaces of rotation having respectively mutually inclined axes in the coronal plane of the head. In the simplest form of such an approximation there are two surfaces of rotation which meet in the region of maximum curvature of the scar as seen in FIG. 1.

Figure 7:
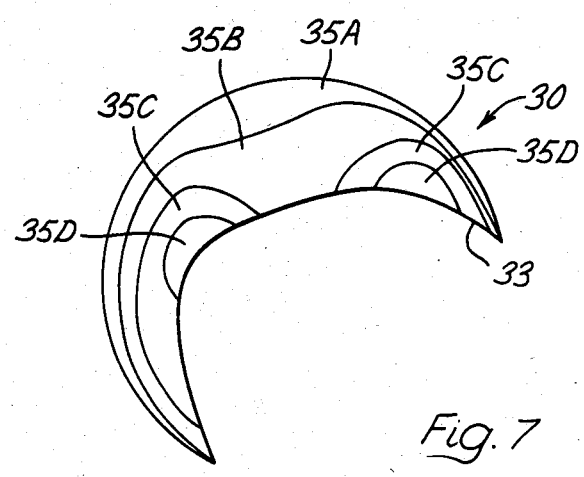
Figure 8:
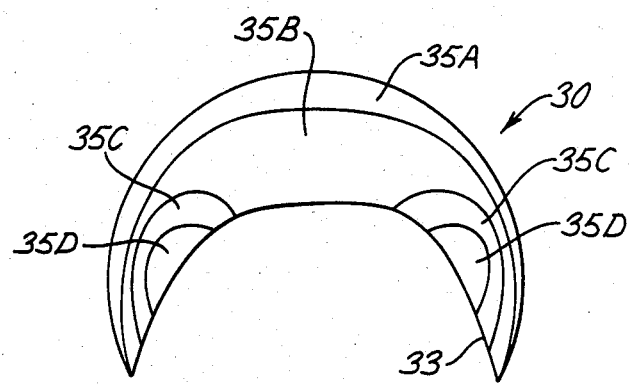

The component of FIGS. 7 and 8 involves the use of a plastics material which can be produced in mouldable forms giving, when set, different elastic moduli. For convenience in this Figure the same reference numerals are used for corresponding elements as in FIGS. 5 and 6 but with the addition of ten. However, numeral 35A, 35B, etc. in this case represent the relevant material with respectively different elastic moduli which successively decrease through the above-mentioned overall range, the different material regions being moulded in sequence to produce the inner part 31 with an overall pattern of modulus variation simulating that indicated in FIGS. 3 and 4. A two-part component construction and filamentary securement can be employedas in FIGS. 5 and 6 and this is indicated in broken line in FIG. 7.

In an alternative mode of production for the component part of FIGS. 7 and 8 the successive regions are formed by spraying the plastics material in a foamed form with a device operable to vary the constituency, and so the elastic modulus, of the material. This offers the advantage that, although the region may be individually of a substantially uniform elastic modulus, the modulus can be smoothly progressively changed from one region to another.

While the present invention has been described with particular reference to the femoral head it is of course not limited thereby, application being possible more generally to bone joint components and especially to those at the ends of the long bones of the limbs where epiphyseal plate scars occur. Clearly for such more general application, data as to trabecullar structure and epiphyseal plate scar form is necessary, but such data is either already available in the literature or is readily obtained by way of existing radiography and other techniques. For example, in the case of the femur at the knee joint the scar has a general shape which undulates circumferentially about its centre, with the undulations being of progressively increasing amplitude in a radial sense. This shape is particularly well suited to torque resistance and for this reason will be beneficial in application to a femoral knee component.

Also, application of the invention is not intended to be limited to the modes of construction as described for the illustrated embodiments. For example, in one alternative, which is similar in general approach to that of FIGS. 5 and 6, use can be made of carbon-fibre-reinforced-carbon, the carbon fibre reinforcement being made up generally to represent the trabecullar structure, then being pyrolised following impregnation with a resin or other binder, and finally being subjected to carbon vapour deposition. Such fabrication is well suited to the production of an inner part with the desired modulus variation and can also be used to provide the high modulus outer part. A further benefit is that the material is porous, the porosity can be controlled, and so allowance can be made for tissue in-growth with the possiblity of such tissue assuming an ossified form at the component-bone junction and a fibro-cartilagenic form over the articular surface.

I claim:

1. A prosthetic component for replacing a condylar region of a long bone including an articular surface of a joint, said component being dimensioned to interface with a resected bone surface of said condylar region of said long bone, said component having a first outer surface shaped to approximate said articular surface and a second inner surface contoured to approximate the fused epiphyseal plate scar contour of said condylar region, wherein upon implantation, said second surface is substantially orthogonal to the principal trabecullar groups with which said second surface interfaces in said condylar region.

2. A component according to claim 1 having, at least in the portion thereof bordering said second surface, a varying elastic modulus configuration to simulate that of the bone material to be replaced thereby.

3. A component according to claim 2 wherein said portion is provided by a body of generally uniform elastic modulus reinforced with fibres of higher elastic modulus, said fibres being disposed in a similar pattern to said trabecullar structure.

4. A component according to claim 2 wherein said portion is provided by a body composed of a plurality of adjoining zones having individually substantially uniform elastic modulus.

5. A component according to claim 4 wherein the elastic modulus is smoothly varied between adjoining zones.

6. A component according to claim 1 of two-part form including a main part defining said second surface, and a shell part connectable with said main part to define said first surface.

7. A component according to claim 6 wherein said main part is formed with a plurality of passageways therethrough for receipt of bone-penetrating securement filaments.

8. A component according to claim 1 for the femoral head at the hip joint wherein said first surface is spherically shaped and said second surface is defined by a succession of different surfaces of rotation having respectively mutually inclined axes in the coronal plane.

* * * * *